(12) United States Patent
Korhonen et al.

(10) Patent No.: US 11,925,762 B2
(45) Date of Patent: Mar. 12, 2024

(54) PORTABLE INHALATOR DEVICE

(71) Applicant: CoreFOX Oy, Salo (FI)

(72) Inventors: Kimmo Korhonen, Salo (FI); Alex Kivikoski, Turku (FI); Mika Hakala, Isokyrö (FI); Tero Kuusinen, Kuusisto (FI); Vesa Luukkanen, Tupos (FI); Jarmo Lähteenmäki, Helsinki (FI); Johanna Nordblad, Helsinki (FI); Mika Saari, Espoo (FI); Petri Soronen, Oulu (FI)

(73) Assignee: COREFOX OY, Salo (FI)

( * ) Notice: Subject to any disclaimer, the term of this patent is extended or adjusted under 35 U.S.C. 154(b) by 489 days.

(21) Appl. No.: 16/028,595

(22) Filed: Jul. 6, 2018

(65) Prior Publication Data

US 2019/0134339 A1    May 9, 2019

(51) Int. Cl.
*A61M 15/00*    (2006.01)
*A61B 5/00*    (2006.01)
(Continued)

(52) U.S. Cl.
CPC ............. *A61M 16/10* (2013.01); *A61B 5/082* (2013.01); *A61B 5/087* (2013.01); *A61B 5/0871* (2013.01); *A61B 5/4839* (2013.01); *A61M 15/00* (2013.01); *A61M 15/0021* (2014.02); *A61M 15/0066* (2014.02); *A61M 16/024* (2017.08); *G16H 20/10* (2018.01); *G16H 20/40* (2018.01); *G16Z 99/00* (2019.02); *A61B 5/0022* (2013.01); *A61M 15/0003* (2014.02); *A61M 15/008* (2014.02); *A61M 2016/0018* (2013.01); *A61M 2016/0021* (2013.01); *A61M 2016/0027* (2013.01);
(Continued)

(58) Field of Classification Search
CPC .... A61M 15/00–0011; A61M 15/0028; A61M 15/0065–0078; A61M 15/0085; A61M 15/009; A61M 15/0091; A61M 15/0093; A61M 15/06; A61M 15/08; A61M 15/085; A61M 11/00; A61M 11/001–008; A61M 11/02–08; A61M 13/00; A24F 40/00–40; A24F 40/50–65
See application file for complete search history.

(56) References Cited

U.S. PATENT DOCUMENTS 5,518,002 A * 5/1996 Wolf .................... A61B 5/0878
482/13
2003/0230303 A1* 12/2003 Nichols ................. A61M 15/00
128/200.14
(Continued)

FOREIGN PATENT DOCUMENTS

WO    WO-2018107018 A1 *    6/2018    ............. A61B 5/087

*Primary Examiner* — Michael J Tsai
(74) *Attorney, Agent, or Firm* — Ziegler IP Law Group, LLC

(57) ABSTRACT

A portable inhalator device includes a housing with a mouthpiece for a user; a gas conduit coupled to the mouthpiece and configured to guide inhaling and exhaling gas flow within the device; a pressure sensor configured to monitor the gas flow in the gas conduit and to provide pressure differential signal for indicating direction of the gas flow through the gas conduit; a detection sensor configured to monitor the gas flow in the gas conduit and to provide characteristics signal for indicating composition of the gas flow through the gas conduit; and a dispenser configured to dispense a drug to the gas conduit.

19 Claims, 4 Drawing Sheets

(51) Int. Cl.
  *A61B 5/08*    (2006.01)
  *A61B 5/087*   (2006.01)
  *A61M 16/00*   (2006.01)
  *A61M 16/10*   (2006.01)
  *G16H 20/10*   (2018.01)
  *G16H 20/40*   (2018.01)
  *G16Z 99/00*   (2019.01)

(52) U.S. Cl.
  CPC ........... *A61M 2016/0036* (2013.01); *A61M 2016/102* (2013.01); *A61M 2205/3303* (2013.01); *A61M 2205/3334* (2013.01); *A61M 2205/3375* (2013.01); *A61M 2205/3553* (2013.01); *A61M 2205/3561* (2013.01); *A61M 2205/3584* (2013.01); *A61M 2205/3592* (2013.01); *A61M 2205/502* (2013.01); *A61M 2205/505* (2013.01); *A61M 2205/52* (2013.01); *A61M 2205/6009* (2013.01); *A61M 2205/6054* (2013.01); *A61M 2205/80* (2013.01); *A61M 2205/8206* (2013.01); *A61M 2205/8237* (2013.01); *A61M 2230/40* (2013.01); *A61M 2230/43* (2013.01)

(56) References Cited

U.S. PATENT DOCUMENTS

| | | | | |
|---|---|---|---|---|
| 2009/0025718 | A1* | 1/2009 | Denyer | A61M 11/005 |
| | | | | 128/203.14 |
| 2010/0089394 | A1* | 4/2010 | Sakurada | A61B 5/4839 |
| | | | | 128/203.14 |
| 2013/0284165 | A1* | 10/2013 | Krimsky | A61M 16/08 |
| | | | | 128/200.14 |
| 2015/0283339 | A1* | 10/2015 | Mahadevan | A61M 16/12 |
| | | | | 128/203.14 |

* cited by examiner

PORTABLE INHALATOR DEVICE

TECHNICAL FIELD

The present application generally relates to a portable inhalator device, especially for dispensing medication for a patient.

BACKGROUND

This section illustrates useful background information without admission of any technique described herein representative of the state of the art.

Various diseases and disorders may be treatable with inhaled medication or substances. For example, a lung disease may cause narrowing of the airways that result in obstructions and a reduction in the volume of air obtained by the patient. Relieving such obstruction may enable easier breathing for the patient and a greater volume of fresh air that reaches the air sacs of the lungs.

A solution is needed to improve dosing of a substance for the user, analysing the effect of the substance and assisting the inhaling procedure.

SUMMARY

Various aspects of examples of the disclosed embodiments are set out in the claims.

According to a first example aspect of the present disclosure, there is provided a portable inhalator device comprising:
- a housing comprising a mouthpiece for a user;
- a gas conduit coupled to the mouthpiece and configured to guide inhaling and exhaling gas flow within the device;
- a pressure sensor configured to monitor the gas flow in the gas conduit and to provide pressure differential signal for indicating direction of the gas flow through the gas conduit;
- a detection sensor configured to monitor the gas flow in the gas conduit and to provide characteristics signal for indicating composition of the gas flow through the gas conduit;
- a dispenser configured to dispense a drug to the gas conduit;
- at least one memory including computer program code; the at least one memory and the computer program code configured to, with the at least one processor, cause the device to:
  receive the pressure differential signal from the pressure sensor;
  determine dispense control information based on the pressure differential signal, the dispense control information comprising at least one of the following:
  timing of dispense; and
  amount of the drug to be dispensed;
  control the dispenser to dispense the drug to the gas conduit based on the dispense control information;
  receive the characteristics signal from the detection sensor;
  determine adjusted control information based on the characteristics signal; and
  adjust the dispenser to dispense the drug to the gas conduit based on the adjusted control information.

In an embodiment, the at least one memory and the computer program code are further configured to, with the at least one processor, cause the device to:
determine negative values for the pressure differential signal for indicating inhalation of the gas flow through the gas conduit.

In an embodiment, the at least one memory and the computer program code are further configured to, with the at least one processor, cause the device to:
determine positive values for the pressure differential signal for indicating exhalation of the gas flow through the gas conduit.

In an embodiment, the at least one memory and the computer program code are further configured to, with the at least one processor, cause the device to:
determine peak expiratory flow (PEF) information based on the positive values of the pressure differential signal.

In an embodiment, the portable inhalator device further comprises a drug container, wherein the drug container is operationally connected to the dispenser for conveying the drug between the drug container and the dispenser.

In an embodiment, the portable inhalator device further comprises a plurality of drug containers, wherein the drug containers are operationally connected to the dispenser for conveying drugs between the plurality of drug containers and the dispenser.

In an embodiment, the at least one memory and the computer program code are further configured to, with the at least one processor, cause the device to:
store user history information comprising at least one of the following:
the dispense control information;
the characteristics signal or characteristics information defined based on the characteristics signal; and
the adjusted control information.

In an embodiment, the at least one memory and the computer program code are further configured to, with the at least one processor, cause the device to:
store device history information comprising at least one of the following:
information on amount of the drug dispensed; and
information on amount of the drug remaining.

In an embodiment, the at least one memory and the computer program code are further configured to, with the at least one processor, cause the device to:
receive container information comprising information on amount of drug within the drug container; and
determine amount of remaining drug within the drug container based on the container information and the device history information.

In an embodiment, the portable inhalator device further comprises an inhaling assistance element, wherein the inhaling assistance element is configured to generate additional inhaling gas flow to the gas conduit.

In an embodiment, the at least one memory and the computer program code are further configured to, with the at least one processor, cause the device to:
determine inhaling assistance control information based on the pressure differential signal, the inhaling assistance control information comprising at least one of the following:
timing of inhaling assistance; and
amount of the inhaling assistance; and
control the inhaling assistance element to generate additional inhaling gas flow to the gas conduit based on the inhaling assistance control information.

According to a second example aspect of the present disclosure, there is provided a computer program comprising computer executable program code configured to control a portable inhalator device, wherein the portable inhalator device comprising a housing comprising a mouthpiece for a user; a gas conduit coupled to the mouthpiece and configured to guide inhaling and exhaling gas flow within the device; a pressure sensor configured to monitor the gas flow in the gas conduit and to provide pressure differential signal for indicating direction of the gas flow through the gas conduit; a detection sensor configured to monitor the gas flow in the gas conduit and to provide characteristics signal for indicating composition of the gas flow through the gas conduit; and a dispenser configured to dispense a drug to the gas conduit; when the computer executable program code is executed, to:

receive the pressure differential signal from the pressure sensor;

determine dispense control information based on the pressure differential signal, the dispense control information comprising at least one of the following:

timing of dispense; and amount of the drug to be dispensed;

control the dispenser to dispense the drug to the gas conduit based on the dispense control information;

receive the characteristics signal from the detection sensor;

determine adjusted control information based on the characteristics signal; and adjust the dispenser to dispense the drug to the gas conduit based on the adjusted control information.

According to a third example aspect of the present disclosure, there is provided an apparatus comprising:

a communication interface for transceiving information over a network;

at least one memory including computer program code;

the at least one memory and the computer program code configured to, with the at least one processor, cause the apparatus to:

receive characteristics signal from a detection sensor of a portable inhalator device;

determining adjusted control information based on the characteristics signal; and transmitting the adjusted control information to the portable inhalator device for adjusting a dispenser to dispense drug to a gas conduit based on the adjusted control information.

According to a fourth example aspect of the present disclosure, there is provided a method for a portable inhalator device, wherein the portable inhalator device comprising a housing comprising a mouthpiece for a user; a gas conduit coupled to the mouthpiece and configured to guide inhaling and exhaling gas flow within the device; a pressure sensor configured to monitor the gas flow in the gas conduit and to provide pressure differential signal for indicating direction of the gas flow through the gas conduit; a detection sensor configured to monitor the gas flow in the gas conduit and to provide characteristics signal for indicating composition of the gas flow through the gas conduit; and a dispenser configured to dispense a drug to the gas conduit; the method comprising:

receiving the pressure differential signal from the pressure sensor;

determining dispense control information based on the pressure differential signal, the dispense control information comprising at least one of the following:

timing of dispense; and amount of the drug to be dispensed;

controlling the dispenser to dispense the drug to the gas conduit based on the dispense control information;

receiving the characteristics signal from the detection sensor;

determining adjusted control information based on the characteristics signal; and adjusting the dispenser to dispense the drug to the gas conduit based on the adjusted control information.

In an embodiment, the method further comprises:

generating patient trauma information based on the characteristics signal;

transmitting the patient trauma information to a server apparatus;

generating patient rehabilitation information based on the patient trauma information;

associating the patient trauma information and the patient rehabilitation information with a patient identifier to provide a collaborative patient record;

automatically determining adjusted control information based on the collaborative patient record; and transmitting the adjusted control information for the portable inhalator device.

In an embodiment, the method further comprises:

transmitting the characteristics signal to a server apparatus;

generating patient trauma information based on the characteristics signal;

generating patient rehabilitation information based on the patient trauma information;

associating the patient trauma information and the patient rehabilitation information with a patient identifier to provide a collaborative patient record;

automatically determining adjusted control information based on the collaborative patient record; and transmitting the adjusted control information for the portable inhalator device.

In an embodiment, the method further comprises:

maintaining history data of a plurality of reference collaborative patient records comprising information on rehabilitation times for different patient traumas;

comparing the received patient trauma information with the history data;

selecting, based on the comparison, at least one reference collaborative patient record; and determining an estimated rehabilitation time for the patient based on the selected reference collaborative patient record and the collaborative patient record.

In an embodiment, the method further comprises:

maintaining history data of a plurality of reference collaborative patient records comprising information on rehabilitation times for different patient traumas;

comparing the received patient trauma information with the history data;

selecting, based on the comparison, at least one reference collaborative patient record; and determining, based on the selected reference collaborative patient record and the collaborative patient record, selection for at least one drug and amount of the drug to be dispensed to be added to the collaborative patient record.

In an embodiment, the method further comprises:

maintaining history data of a plurality of reference collaborative patient records comprising information different patient traumas;

comparing at least one collaborative patient record with the history data;

selecting, based on the comparison, at least one reference collaborative patient record;

determining, based on the selected reference collaborative patient record, preliminary patient trauma information;

providing the preliminary patient trauma information for an approval; and receiving the patient trauma information in response to the approval.

Different non-binding example aspects and embodiments of the present disclosure have been illustrated in the foregoing. The embodiments in the foregoing are used merely to explain selected aspects or steps that may be utilized in implementations of the present invention. Some embodiments may be presented only with reference to certain example aspects of the invention. It should be appreciated that corresponding embodiments may apply to other example aspects as well.

BRIEF DESCRIPTION OF THE DRAWINGS

For a more complete understanding of example embodiments of the present disclosure, reference is now made to the following descriptions taken in connection with the accompanying drawings in which:

FIG. 7b shows a schematic drawing of the second gas conduit part that illustrates an alternative to the venture pipe as shown in FIG. 7a.

DETAILED DESCRIPTION OF THE DRAWINGS

An example embodiment of the present disclosure and its potential advantages are understood by referring to FIGS. 1 through 7b of the drawings. In this document, like reference signs denote like parts or steps.

Figure 1:
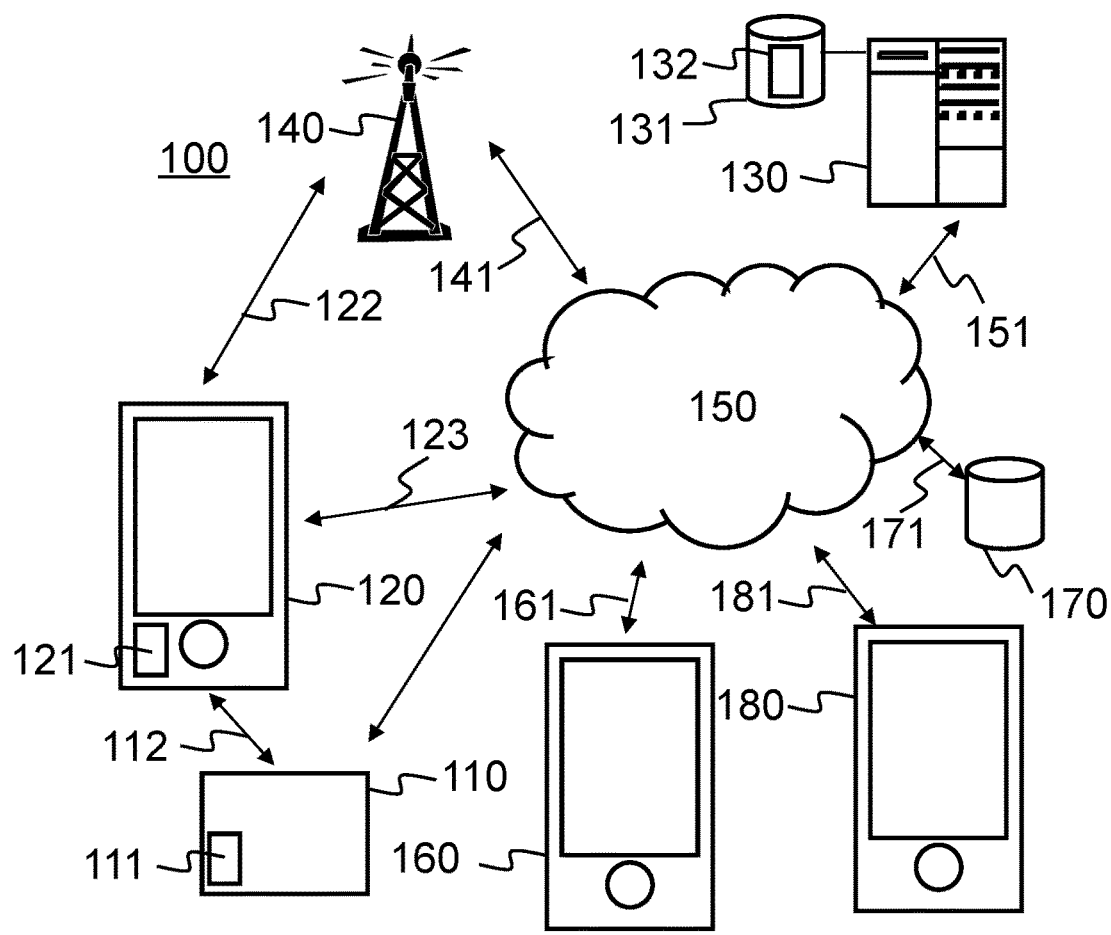
FIG. 1 shows a schematic drawing of a system of an example embodiment.

FIG. 1 shows a schematic picture of a system 100 according to an example embodiment of the invention. The system 100 comprises a portable inhalator device 110 comprising a plurality of sensors. The portable inhalator device 110 is configured to receive the pressure differential signal from a pressure sensor; determine dispense control information based on the pressure differential signal, the dispense control information comprising at least one of the following: timing of dispense; and amount of the drug to be dispensed; control a dispenser to dispense a drug to a gas conduit based on the dispense control information; receive the characteristics signal from a detection sensor; determine adjusted control information based on the characteristics signal; and adjust the dispenser to dispense the drug to the gas conduit based on the adjusted control information.

In an embodiment, the characteristics signal or the pressure differential signal may comprise information of at least one of the following: peak inspiratory flow (PIF), peak expiratory flow (PEF), exhaled nitric oxide (eNO) and audio.

The portable inhalator device 110 may comprise storage 111 for data. The storage 111 may comprise a memory chip or a flash memory card, for example. The portable inhalator device 110 is configured to be connectable to a user apparatus 120 over a data connection 112. The data connection 112 may be a wired connection or a wireless connection. The wired connection may comprise Universal Serial Bus (USB), High-Definition Multimedia Interface (HDMI) or local area network (LAN), for example. The wireless connection may comprise Bluetooth™, Radio Frequency Identification (RF-ID) or wireless local area network (WLAN), for example.

The portable inhalator device 110 is configured to send captured data over the data connection 112 to the user apparatus 120. Such transmittal may be initiated by a user of the portable inhalator device 110, by a user of the user apparatus 120, or automatically based on settings. Such settings may comprise for example time of the day, amount of newly captured data or existence of the data connection 112 for the portable inhalator device 110. The portable inhalator device 110 may further be configured to send captured data over data connection to a server apparatus 130.

The user apparatus 120 may comprise a multimedia device, a mobile phone, an Internet tablet or a laptop computer, for example. The user apparatus 120 is capable of downloading and locally executing software program code. The software program code may be a client application of a service whose server application is running on a server apparatus 130 of the system 100. The user apparatus 120 may comprise user activity capturing element, such as an accelerometer, a module for satellite based global positioning system (e.g. GPS), a module for cellular based positioning system, a module for wireless non-cellular positioning system (e.g. Wi-Fi) or a module for hybrid positioning system, for example.

The user apparatus 120 may also have a metadata element 121 for creating data usable as metadata of the data captured by the portable inhalator device 110. The metadata element 121 may comprise at least one of the following: a microphone, a positioning device for determining the current location of the user apparatus 120, and a clock. The user apparatus 120 is configured to be connectable to a wireless communication network 140 over a wireless connection 122. The wireless connection 122 may comprise a mobile cellular network or a wireless local area network (WLAN), for example. The wireless communication network 140 may be connected to a public data communication network 150, for example to the Internet, over a data connection 141. The client application may be operable also in offline mode and there is no need to have online connection over the network to the server 130, 131 all the time. In offline mode, the user apparatus 120 or user device 110 may store application related data to cache memory and update the data to the server 130, 131 once getting the online access.

Embodiments of the aspects disclose trauma and trauma means in this context any physical, mental or other user body disease, malfunction or disorder.

In an embodiment, a user, for example a patient, may capture data relating to his trauma using a second user apparatus 120 or a portable inhalator device 110. Such data may comprise pressure differential signal from a pressure sensor of the portable inhalator device 110, determined dispense control information based on the pressure differential signal, wherein the dispense control information comprising at least one of the following: timing of dispense; and amount of the drug to be dispensed. Such data may also comprise characteristics signal from a detection sensor or determined adjusted control information based on the characteristics signal. Such data may also comprise multimedia data, such as still images, audio or video stream. The captured data may be sent from the user apparatus 120 to the system server 130. At the system server 130, the received data may be automatically analysed to prepare preliminary patient trauma information, for example. Automatic analysis may comprise, for example, pattern recognition and image recognition, wherein history data of other patients and their data may be used for comparison. Thus, early trauma information may be defined even before the patient visits the doctor.

The patient may be a human or an animal. In case of the animal, an owner of the animal may operate the user apparatus 120 and provide necessary interaction with the system 100.

In an embodiment, the system 100 comprises a server apparatus 130, which comprises a storage device 131 for storing collaborative patient information, such as physical/mental exercise data and/or metadata, such as Internet of Things (IoT) data received over a data connection 151, patient information of users, trauma information of patients, rehabilitation information, training data and diaries, for example. The trauma may comprise a physical or psychological trauma. The collaborative patient information may further comprise descriptive information of physician's/psychologist's diagnose, holistic rehabilitation process description, a large library of audio-visual exercises or tasks, a rehabilitation diary, and nutrition guidance to support the rehabilitation process. The descriptive information for an exercise may comprise instruction information for breathing, for example. The descriptive information for a task may comprise instruction information to capture an image of breakfast items or measuring user's weight, for example.

In an embodiment, the system 100 may further comprise other user apparatuses 160, 180, connected to the network 150 over connections 161, 181 respectively, wherein tasks relating to the service system may be processed. The user apparatus 160 may comprise the user apparatus of a doctor producing the trauma information of a patient, for example. The user apparatus 180 may comprise the user apparatus of a therapist (physical or mental) or pharmacist defining the rehabilitation information of the patient, or pharmacist, based on the trauma information, for example. The user apparatus 120 may comprise the user apparatus of the patient, for example.

In an embodiment, a first user apparatus 160 may be operated by a doctor as a first user. The first user may study, using the first user apparatus 160, service system data maintained in the server apparatus 130 relating to the patient. The data may be saved by the patient before coming to meet the doctor. The data may comprise, for example, information relating to exercises, medicine, sensation of the pain and performance and general comments. The patient data may have been transmitted to the server 130 from the user apparatus 120 and then again, after processing, from the server 130 over data connections 151, 161 and network 150 to the user apparatus 160.

After reviewing the patient data and meeting the patient, the doctor diagnoses patient's trauma and adds patient trauma information to the collaborative patient record maintained in the server 130.

In an embodiment, the doctor may also define or update patient's therapeutic examination and treatment referrals that are automatically saved to the system server 130 for the patient record. Data is immediately visible to all relevant parties, such as therapist, pharmacist, care person, patient, or health care, for example.

Different apparatuses 110, 120, 130, 160, 170, 180 may provide collaborative patient information to be maintained in the service system 100. The collaborative patient information may be maintained as a collaborative patient record 132 within the server apparatus 130, 131. The collaborative patient record 132 may comprise any patient related information provided by different users, the service system or sensors, for example.

Furthermore, the doctor may define rehabilitation targets and recommendations, together with assessing the level of the trauma. The doctor may also add nutrition guides and accept the predefined rehabilitation recommendation for diagnosed trauma. The system service may receive trauma information defined by the doctor as input and provide automatically a predefined proposal for rehabilitation recommendation based on the trauma information. History data of all patients may be used for defining proposed rehabilitation recommendations. The doctor approved patient rehabilitation information is maintained in the collaborative patient record associating the patient trauma information and the patient rehabilitation information with the patient identifier to provide a collaborative patient record.

In an embodiment, a server apparatus 130 maintains, by an operator, the service system data, such as collaborative patient records. The patient records may comprise, for example, patient trauma information, the patient rehabilitation information, and feedback information. Each patient record may be identified using a patient identifier. The patient identifier may comprise, for example a social security number or a personal e-mail address, for example.

Information relating to the collaborative patient records may be transmitted to the server 130 from a plurality of apparatuses 120, 160, 180 over the network 150. Eventually, the received service data is maintained, by an operator, at the server 130 comprising storage device 131, wherein the data being available for users having access to that particular patient record. Furthermore, metadata associated with the service data may also be stored in the server 130 or storage device 131, such as location information, time information, or a device identifier, for example.

In an embodiment, a third user apparatus 180 may be operated by a therapist (physical or mental) or pharmacist. The third user may have an access to the server apparatus 130 and the data available there. The third user may study, using the third user apparatus 180, service system data maintained in the server apparatus 130 relating to the patient. The data may be saved by the patient and the doctor before coming to meet the therapist or pharmacist. The data may comprise, for example, patient trauma information, patient rehabilitation information and information relating to exercises, medicine, sensation of the pain and performance and general comments. The patient data may have been transmitted to the server 130 from the user apparatuses 120, 160 and then again from the server 130 over data connections 151, 161 and network 150 to the user apparatus 180.

The third user, such as the therapist or pharmacist, may also review from the patient record the earlier diagnoses, rehabilitations and recommendations.

After reviewing the patient data and meeting the patient, the therapist or pharmacist examines patient's trauma and adds physical exercises to a dynamic rehabilitation diary defining the physical exercise to be performed in a timely manner and maintaining status of the performance of the physical exercise. The dynamic rehabilitation diary may be comprised by the collaborative patient record available at the server 130. The physical exercises added to the diary may comprise and provide audio-visual training information relating to the selected physical exercises.

In an embodiment, a fourth user may be given access to the collaborative patient record in the server 130. Such fourth user may comprise, for example, a relative, a friend, a care person, a partner or an official linked with the patient, for example.

Any of the user apparatuses 120, 160, 180 may be operated as the first, second or third user apparatus. Same apparatus may also be used as the first, second and third user apparatus.

In an embodiment, patient related data generated by a patient may travel to a server apparatus 130 over different paths. A first path may comprise sending data captured by a proprietary application of a user apparatus 120 over a wireless communication network 122, 140, 141 and public data communication network 150, 151 to the server apparatus 130. A second path may comprise sending data captured by a default application of a user apparatus 120 over a wireless communication network 122, 140, 141 and public data communication network 150, 151 to the server apparatus 130. A third path may comprise sending data captured by an external device 110 (such as running mill or spinning device) to the user apparatus 120 over connection 112 and therefrom over a wireless communication network 122, 140, 141 and public data communication network 150, 151 to the server apparatus 130. A fourth path may comprise sending data captured by the device 110 to a computer apparatus 120 and therefrom over the connection 123 and the public data communication network 150, 151 to the server apparatus 130.

In an embodiment, the server apparatus 130 may be configured to generate risk map information to a healthcare professional based on the patient related data, symptom data, crowd sourced other patients' data, and metadata for available data sources, for example.

In an embodiment, the proprietary application in the user apparatus 120 may be a client application of a service whose server application is running on the server apparatus 130 of the system 100. The proprietary application may capture the data for the first path. Also metadata for the captured data may be retrieved by the proprietary application from the metadata elements 121 of the user apparatus 120. The default application may be an exercising application of the user apparatus 120. For the second path, the data captured by the default application may be imported to the proprietary application before transmitting to the server apparatus 130. The proprietary application may check the data and extract and apply metadata for the data. For the third path, the data may be captured by the external device 110 and transmitted to the proprietary application of the user apparatus 120 for sending to the server apparatus 130. The proprietary application may check the data and extract and apply metadata for the captured data. User may provide additional metadata using the user apparatus 120. For the fourth path, the data may be captured by the external device 110 and transmitted to a communication application of a computer apparatus 120. The communication application may check the captured data and extract and apply metadata for the captured data. User may provide additional metadata using the computer apparatus. In a further embodiment, the user may access the data on the server apparatus and provide additional metadata.

In an embodiment, a proprietary or client application in the user apparatus 160 (e.g. doctor apparatus) defining the trauma information may be a client application of a service whose server application is running on the server apparatus 130 of the system 100. The proprietary application may also be utilized for setting rehabilitation information. Furthermore, the client application may be used to amend the stored data and settings later on.

In an embodiment, a proprietary or client application in the user apparatus 180 (e.g. therapist or pharmacist apparatus) defining and amending rehabilitation information may be a client application of a service whose server application is running on the server apparatus 130 of the system 100. Furthermore, the client application may be used to amend the data and settings later on.

In an embodiment, the external device 110 may comprise a portable inhalator device communicating with the apparatus 120 over a local connection 112. The local connection 112 may comprise, for example, at least one of the Bluetooth, Radio Frequency Identification (RF-ID), near field communication (NFC) or other wireless non-cellular connection. The wireless non-cellular connection may comprise industrial, scientific and medical (ISM) radio bands that are radio bands (portions of the radio spectrum) reserved internationally for the use of radio frequency (RF) energy for industrial, scientific and medical purposes, for example. Alternatively, the portable inhalator device 110 may be comprised by the apparatus 120, as illustrated by an integrated apparatus 121. The apparatus 110, 120, 121 may be for example a wearable user apparatus.

In an embodiment, a communication interface module of the apparatus 120 may comprise location modules for tracking location of the portable apparatus 120. Such location modules may comprise a module for providing a connection to satellite based global positioning system (e.g. GPS, not shown), a module for cellular based positioning system, a module for wireless non-cellular positioning system (e.g. Wi-Fi) or a module for hybrid positioning system, for example. The positioning system may also be used for user speed detection, altitude detection, route detection and route planning for various embodiments.

In an embodiment, the apparatus 120 may be connected over a wireless or wired connection to a wide area network 150, such as Internet. Router apparatuses (not shown) may be used for providing the access to a wide area network 150. The access may comprise cellular or non-cellular connection.

In an embodiment, a proprietary application in the apparatus 120 may be a client application of a service whose server application is running on the server apparatus 130 of the system 100. The proprietary application may capture the user input data for the service and provide the user output data, for the service.

In an embodiment, history data of users, portable inhalator devices, trauma information and rehabilitation information may be maintained at the server 130.

The server 130 may also provide a cloud service for the portable apparatus 120 data. Optionally, further apparatuses may be added, such as peripheral devices for maintaining, providing or processing the portable apparatus 120 data and communication devices for connecting the peripheral devices to the system 100.

The system 100 for providing collaborative patient information may comprise rehabilitation ecosystem (global and local), where the patient (user apparatus 120) is in the middle of healthcare process, software (core SW at server apparatus 130) that enables interactive communication between patient (user apparatus 120) and healthcare professionals (user apparatuses 160, 180), application software (browser SW in apparatuses 160, 180) tool for healthcare professionals to provide rehabilitation program to patient apparatuses 110, 120 and to monitor patient rehabilitation progress, application software (mobile SW in apparatuses 110, 120) for patient self-rehabilitation and on-line communication with healthcare professionals, a camera application for recording additional personalized exercises by the user apparatus 180 and an editing software tool for providing personal exercise descriptions.

In an embodiment, the system 100 may further comprise an external database 170. The external database 170 may comprise patient information, rehabilitation information, trauma information, history data, estimate information or such, maintained by another service provider that the service system provider of server 130, 131. The database 170 may be accessible to the network 150 over connection 171. The database 170 may have corresponding structure as the server apparatus 130, 131, for example. The external database 170 may comprise, for example, public healthcare service data server from where patient related data may be received. Furthermore, the external database 170 may also comprise, for example, third party service provider, such as an insurance company that may receive patient or rehabilitation related data from the server 130, 131.

In an embodiment, the portable inhalator device 110 enables generating, transmitting and prioritizing health data to a public or private healthcare system. At the same time more accurate, easier, faster and dynamic system is provided between the patient and a doctor/therapist/authorized caretaker or such. Instructions and orders for medication, physical exercises, diet, or mental training may be dynamically adjusted and updated based on the data initially generated by the portable inhalator device 110.

Figure 2:
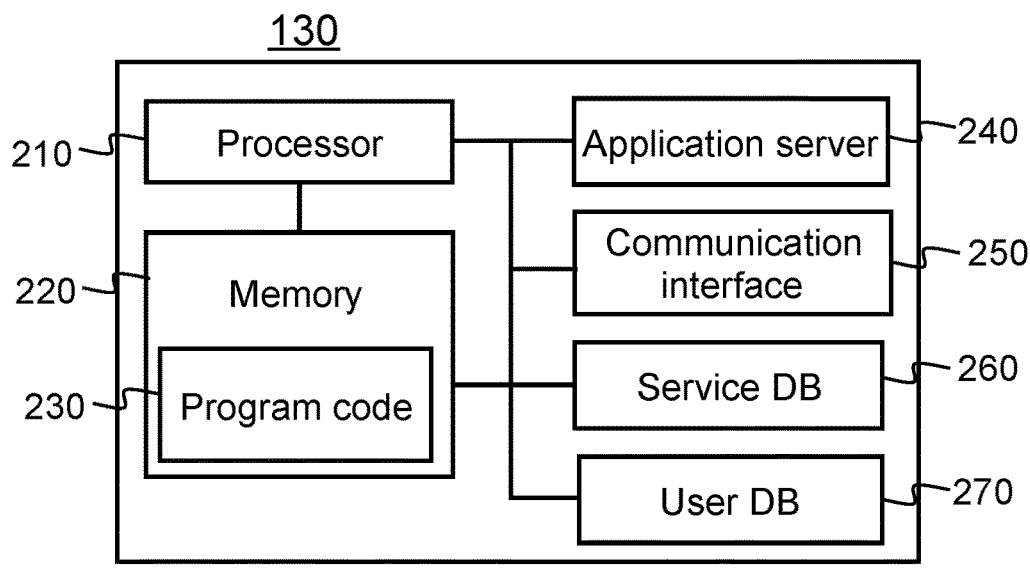
FIG. 2 shows a block diagram of the server apparatus of an example embodiment.

FIG. 2 presents an example block diagram of a server apparatus 130 in which various embodiments of the invention may be applied. All elements described in FIG. 2 are not necessary to be implemented in the same apparatus 130.

The general structure of the server apparatus 130 comprises a processor 210, and a memory 220 coupled to the processor 210. The server apparatus 130 further comprises software 230 stored in the memory 220 and operable to be loaded into and executed in the processor 210. The software 230 may comprise one or more software modules and can be in the form of a computer program product.

The processor 210 may be, e.g., a central processing unit (CPU), a microprocessor, a digital signal processor (DSP), a graphics processing unit, or the like. FIG. 2 shows one processor 210, but the server apparatus 130 may comprise a plurality of processors.

The memory 220 may be for example a non-volatile or a volatile memory, such as a read-only memory (ROM), a programmable read-only memory (PROM), erasable programmable read-only memory (EPROM), a random-access memory (RAM), a flash memory, a data disk, an optical storage, a magnetic storage, a smart card, or the like. The server apparatus 130 may comprise a plurality of memories. The memory 220 may be constructed as a part of the server apparatus 130 or it may be inserted into a slot, port, or the like of the server apparatus 130 by a user. The memory 220 may serve the sole purpose of storing data, or it may be constructed as a part of an apparatus serving other purposes, such as processing data.

The communication interface module 250 implements at least part of data transmission. The communication interface module 250 may comprise, e.g., a wireless or a wired interface module. The wireless interface may comprise such as a WLAN, Bluetooth, infrared (IR), radio frequency identification (RF ID), GSM/GPRS, CDMA, WCDMA, LTE (Long Term Evolution) or 5G radio module. The wired interface may comprise such as Ethernet or universal serial bus (USB), for example. The communication interface module 250 may be integrated into the server apparatus 130, or into an adapter, card or the like that may be inserted into a suitable slot or port of the server apparatus 130. The communication interface module 250 may support one radio interface technology or a plurality of technologies. Configuration information between the user apparatus 120 and the system server 130 may be transceived using the communication interface 250. Similarly, account creation information between the system server 130 and a service provider may be transceived using the communication interface 250.

An application server 240 provides application services e.g. relating to the user accounts stored in a user database 270 and to the service information stored in a service database 260. Different application services may be provided to different users, such as the first user (doctor), the second user (patient) and the third user (therapist or pharmacist). The service information may comprise patient trauma information, patient rehabilitation information, and patient feedback information, for example.

A skilled person appreciates that in addition to the elements shown in FIG. 2, the server apparatus 130 may comprise other elements, such as microphones, displays, as well as additional circuitry such as input/output (I/O) circuitry, memory chips, application-specific integrated circuits (ASIC), processing circuitry for specific purposes such as source coding/decoding circuitry, channel coding/decoding circuitry, ciphering/deciphering circuitry, and the like. In an embodiment, the apparatus 130 is configured to receive characteristics signal from a detection sensor of a portable inhalator device, determine adjusted control information based on the characteristics signal, and transmit the adjusted control information to the portable inhalator device for adjusting a dispenser to dispense drug to a gas conduit based on the adjusted control information.

In an embodiment, the apparatus 130 is configure to receive feedback information given by a user, such as a patient, from the user apparatus that may relate to rehabilitation the patient is going through according to instructions given by a doctor and/or a therapist (physical or mental) or pharmacist. The rehabilitation information maintained in the system may comprise rehabilitation diary for a plurality of (physical) exercises. It is important that the patient updates feedback relating to the rehabilitation progress to the system and that the responsible doctor and/or the therapist or pharmacist have access to the information as quickly as possible. The feedback information may relate, for example, to performed physical exercises according to the rehabilitation diary, medicines ordered by the doctor, state of swelling, sensation of pain in the rest, sensation of pain in the stress, estimate on general performance and patient's general daily comments and multimedia messages such as voice, video or still images.

Figure 3:
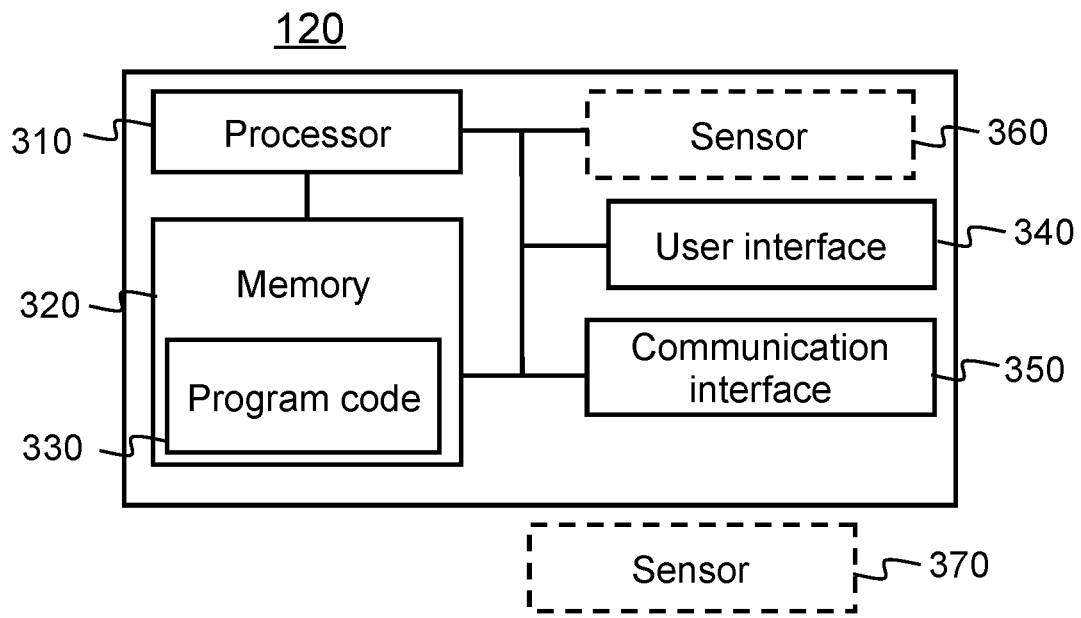
FIG. 3 shows a block diagram of a user apparatus of an example embodiment.

FIG. 3 shows a block diagram of a user apparatus 120 of an example embodiment. In an embodiment, a sensor 360, 370 may be implemented as a separate device 370 (e.g. within a portable inhalator device) communicating via the communication interface 350 with the apparatus 120, or as an integrated sensor 360 within the apparatus 120. The user interface 340 may be implemented also in another device connected via a communication interface 350 to the apparatus 120. Such device may comprise a mobile phone, a smart phone, or a tablet, for example. In an embodiment, the apparatus 120 may communicate with a plurality of sensors 360, 370, both internal and external sensors, and of a plurality of users. In an embodiment, the sensor 360 may also comprise a camera for capturing multimedia data to be submitted to the server apparatus 130, 131 for determination of preliminary trauma information or for creating multimedia data.

The general structure of the apparatus 120 comprises a user interface 340, a communication interface 350, a processor 310, and a memory 320 coupled to the processor 310. The apparatus 120 further comprises software 330 stored in the memory 320 and operable to be loaded into and executed in the processor 310. The software 330 may comprise one or more software modules and can be in the form of a computer program product. Not all elements of FIG. 3 are necessary but optional for the portable apparatus 120, such as the sensor 360, 370.

The processor 310 may be, e.g., a central processing unit (CPU), a microprocessor, a digital signal processor (DSP), a graphics processing unit, or the like. FIG. 3 shows one processor 310, but the apparatus 120 may comprise a plurality of processors.

The memory 320 may be for example a non-volatile or a volatile memory, such as a read-only memory (ROM), a programmable read-only memory (PROM), erasable programmable read-only memory (EPROM), a random-access memory (RAM), a flash memory, a data disk, an optical storage, a magnetic storage, a smart card, or the like. The apparatus 120 may comprise a plurality of memories. The memory 320 may be constructed as a part of the apparatus 120 or it may be inserted into a slot, port, or the like of the apparatus 120 by a user. The memory 320 may serve the sole purpose of storing data, or it may be constructed as a part of an apparatus serving other purposes, such as processing data.

The user interface 340 may comprise circuitry for receiving input from a user of the apparatus 120, e.g., via a keyboard, a touchpad, a motion sensor, a touch-screen of the apparatus 120, speech recognition circuitry, gesture recognition circuitry or an accessory device, such as a headset or a remote controller, for example. Furthermore, the user interface 340 may comprise circuitry for providing output for the user via a display, a speaker, a touch-sensitive display or a tactile feedback device, for example.

In an embodiment, a patient may speak relating to sensations and the speech is automatically converted to feedback information for the system. Thus feedback is always up-to-date and accurate.

The communication interface module 350 implements at least part of data transmission. The communication interface module 350 may comprise, e.g., a wireless or a wired interface module. The wireless interface may comprise such as a WLAN, Bluetooth, infrared (IR), radio frequency identification (RF ID), NFC, GSM/GPRS, CDMA, WCDMA, or LTE (Long Term Evolution) radio module. The wired interface may comprise such as universal serial bus (USB), HDMI, SCART or RCA, for example. The communication interface module 350 may be integrated into the apparatus 120, or into an adapter, card or the like that may be inserted into a suitable slot or port of the apparatus 120. The communication interface module 350 may support one radio interface technology or a plurality of technologies. The communication interface module 350 may support one wired interface technology or a plurality of technologies. The apparatus 120 may comprise a plurality of communication interface modules 350.

In an embodiment, the communication interface module 350 may comprise location modules for tracking location of the apparatus 120. Such location modules may comprise a module for satellite based global positioning system (e.g. GPS), a module for cellular based positioning system, a module for wireless non-cellular positioning system (e.g. Wi-Fi) or a module for hybrid positioning system, for example.

In an embodiment, the communication interface 350 with a satellite based global positioning system (e.g. GPS) may detect altitude of the user to provide an estimate of thinness of air. Such estimate of air thinness may be used as input for determining adjusted control information for the portable inhalator device and dosing drug.

A skilled person appreciates that in addition to the elements shown in FIG. 3, the apparatus 120 may comprise other elements, such as microphones, speakers, sensors, cameras, as well as additional circuitry such as input/output (I/O) circuitry, memory chips, application-specific integrated circuits (ASIC), processing circuitry for specific purposes such as source coding/decoding circuitry, channel coding/decoding circuitry, ciphering/deciphering circuitry, and the like. Additionally, apparatus 120 may comprise a disposable or rechargeable battery (not shown) for powering when external power if external power supply is not available.

In an embodiment, the apparatus 120 comprises speech or gesture recognition means. Using these means, a pre-defined phrase or a gesture may be recognized from the speech or the gesture and translated into control information for the apparatus 120.

Figure 4:
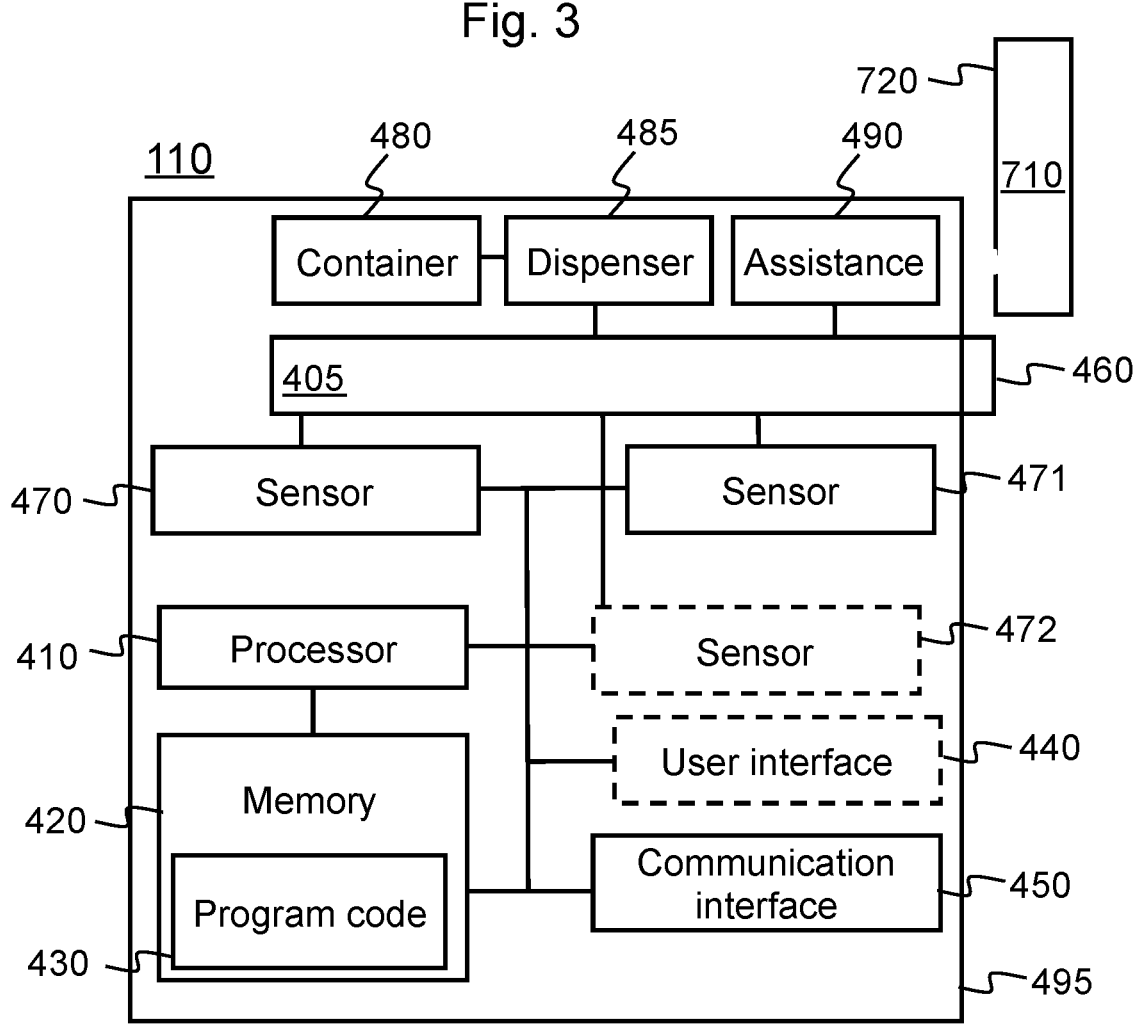
FIG. 4 shows a block diagram of a portable inhalator device of an example embodiment.

FIG. 4 shows a block diagram of a portable inhalator device 110 of an example embodiment. In an embodiment, a plurality of sensors 470-472 is included. At least two sensors 470,471 are implemented. The user interface 440 may be optional and implemented also in another device connected via a communication interface 450 to the device 110. Such device may comprise a mobile phone, a smart phone, or a tablet, for example. In an embodiment, the device 110 may communicate with a plurality of sensors 470-472, both internal and external sensors, and of a plurality of users. In an embodiment, the sensor may also comprise a camera for capturing multimedia data to be submitted to the server apparatus 130, 131 for determination of preliminary trauma information or for creating multimedia data.

The portable inhalator device 110 comprises a housing 495 comprising a mouthpiece 460 for a user and a gas conduit 405 coupled to the mouthpiece 460 and configured to guide inhaling and exhaling gas flow within the device 110.

The portable inhalator device 110 may in some embodiments comprise, an adaptor 720 that is removably attached to the gas conduit part 405 of the device 110. The adaptor 720 may be removable and exchangeable to the device 110 to selectively open or close at least one of the gas conduit parts 405 and the gas conduit status is detected and provided to the service system.

The portable inhalator device 110 further comprises a pressure sensor 470 configured to monitor the gas flow in the gas conduit 405 and to provide pressure differential signal for indicating direction of the gas flow through the gas conduit 405.

In embodiment, the pressure sensor 470 may comprise a plurality of pressure sensors. The pressure sensor(s) 470 are configured to provide direction and volume of the flow that may be used to determine characteristics of breathing and dosing of the drug (timing and amount).

The portable inhalator device 110 further comprises a detection sensor 471 configured to monitor the gas flow in the gas conduit 405 and to provide characteristics signal for indicating composition of the gas flow through the gas conduit 405.

The portable inhalator device 110 further comprises a dispenser 485 configured to dispense a drug to the gas conduit 405.

The portable inhalator device 110 further comprises at least one memory 420 including computer program code 430; the at least one memory 420 and the computer program code 430 configured to, with the at least one processor 410, cause the device 110 to:
- receive the pressure differential signal from the pressure sensor 470;
- determine dispense control information based on the pressure differential signal, the dispense control information comprising at least one of the following:
  - timing of dispense; and
  - amount of the drug to be dispensed;
- control the dispenser 485 to dispense the drug to the gas conduit 405 based on the dispense control information;
- receive the characteristics signal from the detection sensor 471;
- determine adjusted control information based on the characteristics signal; and
- adjust the dispenser 485 to dispense the drug to the gas conduit 405 based on the adjusted control information.

In an embodiment, the portable inhalator device 110 further comprises an inhaling assistance element 490, wherein the inhaling assistance element 490 is configured to generate additional inhaling gas flow to the gas conduit 405.

In an embodiment, the portable inhalator device 110 further comprises a drug container 480, wherein the drug container 480 is operationally connected to the dispenser 485 for conveying the drug between the drug container 480 and the dispenser 485.

In an embodiment, the portable inhalator device 110 may comprise a plurality of drug containers 480, wherein the drug containers 480 are operationally connected to the dispenser for conveying drugs between the plurality of drug containers 480 and the dispenser 485.

No matter elements 480-490 are not connected in FIG. 4 to other elements than the gas conduit 405, they may be connected to any other element 410-472.

The general structure of the portable inhalator device 110 may comprise a user interface 440, a communication interface 450, a processor 410, and a memory 420 coupled to the processor 410. The portable inhalator device 110 further comprises software 430 stored in the memory 420 and operable to be loaded into and executed in the processor 410. The software 430 may comprise one or more software modules and can be in the form of a computer program product. Not all elements of FIG. 4 are necessary but optional for the portable inhalator device 110, such as the sensor 472 and the user interface 440.

The processor 410 may be, e.g., a central processing unit (CPU), a microprocessor, a digital signal processor (DSP), a graphics processing unit, or the like. FIG. 4 shows one processor 410, but the portable inhalator device 110 may comprise a plurality of processors.

The memory 420 may be for example a non-volatile or a volatile memory, such as a read-only memory (ROM), a programmable read-only memory (PROM), erasable programmable read-only memory (EPROM), a random-access memory (RAM), a flash memory, a data disk, an optical storage, a magnetic storage, a smart card, or the like. The portable inhalator device 110 may comprise a plurality of memories. The memory 420 may be constructed as a part of the portable inhalator device 110 or it may be inserted into a slot, port, or the like of the portable inhalator device 110 by a user. The memory 420 may serve the sole purpose of storing data, or it may be constructed as a part of an apparatus serving other purposes, such as processing data.

The user interface 440 may comprise circuitry for receiving input from a user of the portable inhalator device 110, e.g., via a keyboard, a touchpad, a motion sensor, a touchscreen of the portable inhalator device 110, speech recognition circuitry, gesture recognition circuitry or an accessory device, such as a headset or a remote controller, for example. Furthermore, the user interface 440 may comprise circuitry for providing output for the user via a display, a speaker, a touch-sensitive display or a tactile feedback device, for example.

In an embodiment, a patient may speak relating to sensations and the speech is automatically converted to feedback information for the system. Thus feedback is always up-to-date and accurate.

The communication interface module 450 implements at least part of data transmission. The communication interface module 450 may comprise, e.g., a wireless or a wired interface module. The wireless interface may comprise such as a WLAN, Bluetooth, infrared (IR), radio frequency identification (RF ID), NFC, GSM/GPRS, CDMA, WCDMA, LTE (Long Term Evolution), or 5G radio module. The wired interface may comprise such as universal serial bus (USB), HDMI, SCART or RCA, for example. The communication interface module 450 may be integrated into the portable inhalator device 110, or into an adapter, card or the like that may be inserted into a suitable slot or port of the portable inhalator device 110. The communication interface module 450 may support one radio interface technology or a plurality of technologies. The communication interface module 450 may support one wired interface technology or a plurality of technologies. The portable inhalator device 110 may comprise a plurality of communication interface modules 450.

In an embodiment, the communication interface module 450 may comprise location modules for tracking location of the portable inhalator device 110. Such location modules may comprise a module for satellite based global positioning system (e.g. GPS), a module for cellular based positioning system, a module for wireless non-cellular positioning system (e.g. Wi-Fi) or a module for hybrid positioning system, for example.

In an embodiment, the communication interface 450 with a satellite based global positioning system (e.g. GPS) may detect altitude of the user to provide an estimate of thinness of air. Such estimate of air thinness may be used as input for determining adjusted control information for the portable inhalator device and dosing drug.

A skilled person appreciates that in addition to the elements shown in FIG. 4, the portable inhalator device 110 may comprise other elements, such as microphones, speakers, sensors, cameras, as well as additional circuitry such as input/output (I/O) circuitry, memory chips, application-specific integrated circuits (ASIC), processing circuitry for specific purposes such as source coding/decoding circuitry, channel coding/decoding circuitry, ciphering/deciphering circuitry, and the like. Additionally, the portable inhalator device 110 may comprise a disposable or rechargeable battery (not shown) for powering when external power if external power supply is not available.

In an embodiment, the portable inhalator device 110 comprises speech or gesture recognition means. Using these means, a pre-defined phrase or a gesture may be recognized from the speech or the gesture and translated into control information for the portable inhalator device 110.

The portable inhalator device 110 is configured to provide two-direction flow measurement combined with a drug doser arrangement. This makes it possible to measure effectiveness of drug dosing and influence of the dosed drug (detection sensor 471) and to measure, for example, the peak expiratory flow (PEF) (pressure sensor 470).

The portable inhalator device 110 may also be configured to measure (PIF) peak inspiratory flow.

In an embodiment, a detection sensor 471 is configured to monitor the gas flow in the gas conduit and to provide characteristics signal for indicating composition of the gas flow in view of diagnosing a disease, impurities or infection within a body system of the patient.

Furthermore, it is possible to adjust drug dosing of the dispenser 485 based on measured parameters, both the amount of drug and timing of the dosing (e.g. using sensor 472).

Number of drug dosing activities, times, locations may be detected and stored. Amount of remaining drug in the container 480 may be determined by calculating the amount of dosed drug in view of total amount of drug of the container 480 when installed. Automatic alert of drug amount and ordering more drug may be provided by the device 110 and/or the user apparatus 120.

In an embodiment, assistive inhaling flow may be provided by the assistant inhaling element 490 (e.g. using sensor 472). By timing the assistive inhaling flow and power of it improves the delivery of the drug into the patient lungs, for example.

In an embodiment, the portable inhalator device 110 may be charged wirelessly.

In an embodiment, a microphone is included within the portable inhalator device 110. The microphone may be within any of the sensors 470-471 or within the user interface 440, for example. The microphone may be used to determine the timing of the dosing, analysing the dosing procedure and characteristics of it or to monitor patient actions during night-time or during a disorder, for example.

One use case carried out using the portable inhalator device 110 may be diagnosis of chronic obstructive pulmonary disease (COPD) based on detected shortness of breath, sputum production, or spirometry measurements. The spirometry measurements may comprise measurements, based on sensors 470-472 of the amount of airflow obstruction present and is generally carried out after the use of a bronchodilator, a medication to open up the airways. The bronchodilator may first be dosed using the dispenser 485 and the container 480, possibly with the aid of the assistance 490. Two main components are measured to make the diagnosis: the forced expiratory volume in one second (FEV1), which is the greatest volume of air that can be breathed out in the first second of a breath, and the forced vital capacity (FVC), which is the greatest volume of air that can be breathed out in a single large breath. Normally, 75-80% of the FVC comes out in the first second and a FEV1/FVC ratio of less than 70% in someone with symptoms of COPD defines a person as having the disease. Evidence for using spirometry among those without symptoms in an effort to diagnose the condition earlier is of uncertain effect and is therefore currently not recommended.

A peak expiratory flow (the maximum speed of expiration), commonly used in asthma, is not sufficient for the diagnosis of COPD.

In an embodiment, user history information, such as the dispense control information; the characteristics signal or characteristics information defined based on the characteristics signal; and the adjusted control information may be stored. Also, device history information, such as information on amount of the drug dispensed; and information on amount of the drug remaining, may be stored. Container information comprising information on amount of drug within the drug container may be received; and amount of remaining drug within the drug container determined based on the container information and the device history information.

Inhaling assistance control information may be determined based on the pressure differential signal, the inhaling assistance control information comprising at least one of the following: timing of inhaling assistance; and amount of the inhaling assistance; and the inhaling assistance element is controlled to generate additional inhaling gas flow to the gas conduit based on the inhaling assistance control information.

Figure 5:
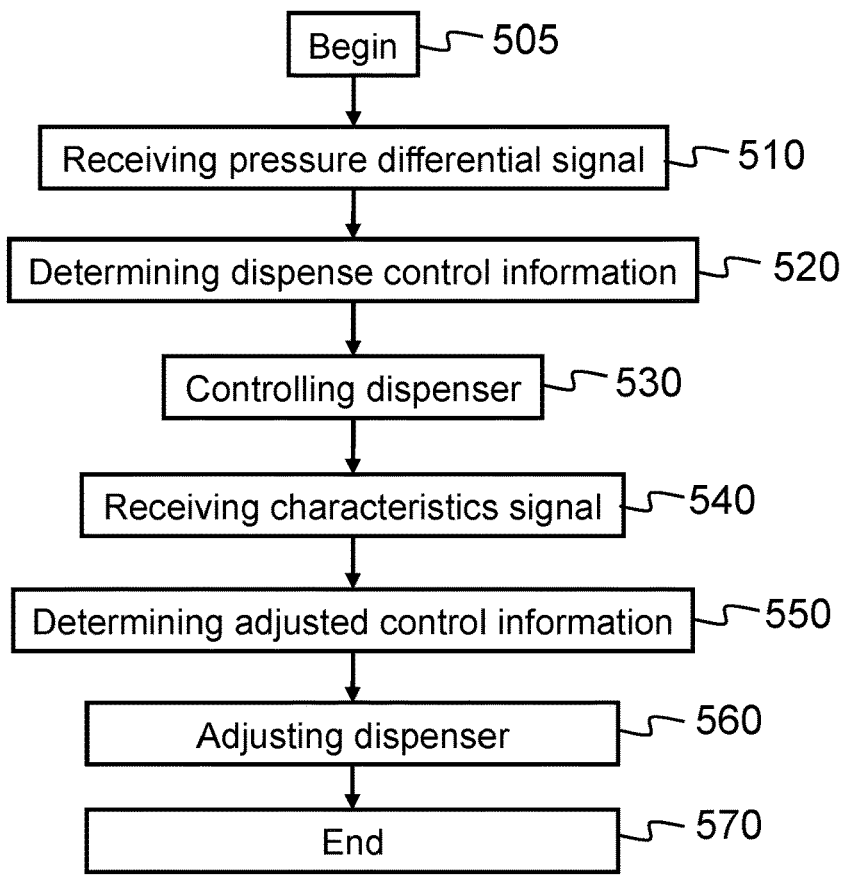
FIG. 5 shows a flow chart of a process according to another example embodiment.

FIG. 5 shows a flow chart of a process according to another example embodiment of the present disclosure.

The process starts at step 505 involving a portable inhalator device, wherein the portable inhalator device comprises a housing comprising a mouthpiece for a user; a gas conduit coupled to the mouthpiece and configured to guide inhaling and exhaling gas flow within the device; a pressure sensor configured to monitor the gas flow in the gas conduit and to provide pressure differential signal for indicating direction of the gas flow through the gas conduit; a detection sensor configured to monitor the gas flow in the gas conduit and to provide characteristics signal for indicating composition of the gas flow through the gas conduit; and a dispenser configured to dispense a drug to the gas conduit.

At step 510, the pressure differential signal is received from the pressure sensor.

At step 520, dispense control information is determined based on the pressure differential signal, wherein the dispense control information comprises at least one of the following:

timing of dispense; and amount of the drug to be dispensed.

At step 530, the dispenser is controlled to dispense the drug to the gas conduit based on the dispense control information.

At step 540, the characteristics signal is received from the detection sensor.

At step 550, adjusted control information is determined based on the characteristics signal.

At step 560, the dispenser is adjusted to dispense the drug to the gas conduit based on the adjusted control information.

At step 570, the process ends.

Before step 570 of the process, the patient may transmit feedback information to the system server relating to the drug dosing effectiveness and the feedback information is added to the collaborative patient record in the server 130. The feedback information may also comprise any feedback relating to the rehabilitation or patients health status. The feedback may comprise, for example patient's opinion on pain, swelling, sensation/feeling, subjective status and objective status. The subjective status may comprise patient's own estimate of his/her physical or mental health. The objective status may comprise health related data from various sensors, user devices (such as blood pressure measuring device) or laboratory results, for example.

Furthermore, before step 570 of the process, an automatic alert may be determined by the process run in the system using at least one of the following: the patient trauma information, the patient rehabilitation information, the feedback information, and drug container status information.

In an embodiment, the automatic alert is based on the dynamic rehabilitation or inhalator device diary and the automatic alert is sent to a user apparatus of the patient. The automatic alert may also be sent to a user apparatus of a doctor providing the patient trauma information and/or to a user apparatus of a pharmacist providing the drug for at least one container.

In an embodiment, rehabilitation may be followed before step 570. Further feedback for questionnaires may be activated for estimating the status of rehabilitation. Feedback information may be requested after each drug-dosing phase (e.g. physical or mental) being performed based on changed performance status of the exercise in the dynamic rehabilitation diary. Furthermore, the requested feedback comprises a pain scale questionnaire to be answered by the patient.

In an embodiment, after receiving answers to the pain scale questionnaire, the answers are converted to the feedback information relating and the system further adds the feedback information to the collaborative patient record, and the service system may generate a report based on the feedback information.

The feedback information may comprise patient's opinion on pain, swelling, sensation/feeling, subjective status and objective status. The subjective status may comprise patient's own estimate of his/her physical or mental health. The objective status may comprise health related data from various sensors, user devices (such as blood pressure measuring device) or laboratory results, for example.

The report may be sent to a user apparatus of a doctor providing the patient trauma information and/or to a user apparatus of a pharmacist providing the drug.

In an embodiment, the automatic alert to a user apparatus of the patient comprises instructions to perform a drug dosing defined by the dynamic rehabilitation diary or ordering more drug for the container, for example.

Figure 6:
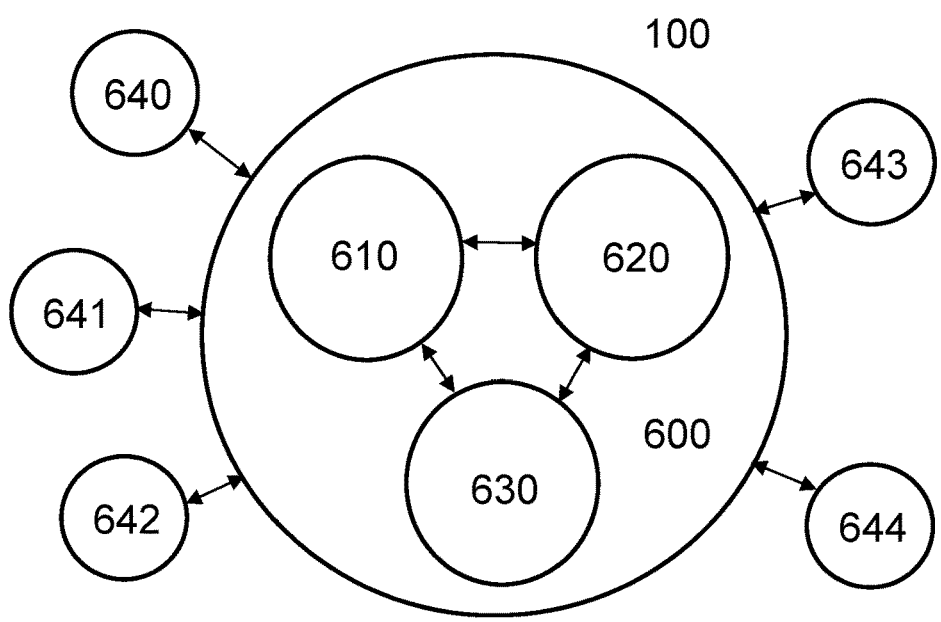
FIG. 6 shows a schematic illustration of different users of the service system according to an embodiment.

FIG. 6 shows a schematic illustration of different users of the service system 100 according to an embodiment. The service system 100 comprises three main users. A first user 610, a second user 620 and a third user 630. The first user 610 may comprise a doctor, the second user 620 may comprise a patient, and the third user 630 may comprise a therapist (physical or mental) or a pharmacist, for example. All three users 610-630 may generate collaborative patient information 600 to be maintained in the service system 100. The collaborative patient information 600 may be maintained as a collaborative patient record within the server 130, 131.

In an embodiment, external users 640-644 may be connected to the service system 100 to have access to at least a pre-defined portion of the collaborative patient information 600. The access for the users 640-644 may be limited to certain patient(s) 620 and/or certain parts of the collaborative patient information 600.

External users may comprise, but are not limited to, a relative 640 of the patient 620, an insurance company 641 of the patient 620, public health care 642 of the patient 620, an employer 643 of the patient 620 or a health care clinic 644 of the patient 620, for example. The relative 640 or a person from health care clinic 644 may comprise a care person 640, 644 that is a dedicated person having access to at least part of the collaborative patient record and looking after the patient trauma and rehabilitation.

In an embodiment the relative 640 may have access from a remote user apparatus, corresponding to at least one of the user apparatuses 120, 160, 180 illustrated in FIG. 1, and have access to the collaborative patient information maintained in the system server 130 of the service system 100. The relative user 640 may access information 600 relating to the persons 610, 630 who are part of the patient's 620 treatment. Thus, the relative 640 can contact right persons if needed. The relative user 640 may also access information 600 about the patient trauma to decrease uncertainty and eliminate misunderstanding. The relative user 640 may also access information 600 on how the patient 620 can be rehabilitated back to normal performance. Such information improves relatives' atmosphere and helps to encourage the patient. Access to the information 600 also enables the relative user 640 to follow the patient's rehabilitation progress and reporting. Such following helps the relative user 640 to realize the progress and patient's 620 motivation for the rehabilitation. If the patient 620 can't report of giver feedback information to the system 100, the rehabilitation progress relative 640 can do it for him/her. The relative user 640 may also access information 600 for following the sensation of the pain and recommended diet to better understand and support the patient 620 progress.

In an embodiment the employer user 643 may have access from a remote user apparatus, corresponding to at least one of the user apparatuses 120, 160, 180 illustrated in FIG. 1, and have access to the collaborative patient information maintained in the system server 130 of the service system 100. The employer user 643 may access information 600 about the patient's (employee) trauma to decrease uncertainty and eliminate misunderstanding. The employer user 643 may also have access for information on how the patient can be rehabilitated back to normal performance to make it easier to forecast when employee comes back to work. Furthermore, by following the patient rehabilitation progress and reporting using the system 100, it helps the employer to plan on deputes for the patient. The collaborative patient information 600 may also provide Information of average rehabilitation period duration for the trauma of the patient to help the employer to control health care costs and quality development.

In an embodiment the health care user 642,644 may have access from a remote user apparatus, corresponding to at least one of the user apparatuses 120, 160, 180 illustrated in FIG. 1, and have access to the collaborative patient information maintained in the system server 130 of the service system 100. The health care user 642,644 may access information 600 relating to entire ecosystem (patients of the healthcare, for example) for rehabilitation. Such information produces reliable and real time data for health care operations and helps to define quality improvement. The health care user 642,644 may also have access to real information rehabilitation period and it's progress directly for a certain patient. Such information helps to control health care costs and quality development. Following the patient's rehabilitation progress and reporting provides information of treatment effectiveness, analysis, measuring and reporting. Then again, having access to information 600 relating to sensation of the pain and to the recommended diet provides information of treatment effectiveness for further analysis and creates possibilities for new business. Alerts may be used as well for health care users 642,644 to indicate the users 642,644 if the rehabilitation does not progress according to the plan.

In an embodiment the insurance company user 641 may have access from a remote user apparatus, corresponding to at least one of the user apparatuses 120, 160, 180 illustrated in FIG. 1, and have access to the collaborative patient information maintained in the system server 130 of the service system 100. The insurance company user 641 may access information 600 relating to real time information for the rehabilitation recommendations, periods and progress for different traumas. That provides a possibility to develop new products. The insurance company user 641 may further access information 600 on how patients 620 are rehabilitated. Such access provides reliable information directly for certain patients and improves follow up of rehabilitation effectiveness. The insurance company user 641 may also access information of needed doctor and therapist or pharmacist visits for different traumas to improve estimation of cost claims. The insurance company user 641 may further measure health care users 642,644, rehabilitation partners 630 and other parties involved in the rehabilitation process to improve future partner selections and to increase e-services and their quality, for example.

The service system 100 offers a digital environment where healthcare professionals 610, 630 can interactively communicate with patients 620 and support their needs on-line. In an embodiment, a user (a patient) inhales a medicine from the drug container and simultaneously peak inspiratory flow (PIF) is measured by at least one sensor to define information of drug inhaling. In response to determining by the data processing means that the PIF value (or some other measured value) changes (e.g. weakens), the data processing (either in the portable device 110 or in the cloud server) may request the patient user to perform other measurements, such as PEF, NO and/or audio using the adaptor 720, for example. Thus, holistic objective and subjective (patient) data is generated and such data may be used to generate automated feedback and input to health care systems and processes. Furthermore, automatic selfcare instructions or updates (medicine, training, nutrition) may be generated by the data processing means even without consulting a doctor, or trigger consultation for the doctor.

Figure 7A:
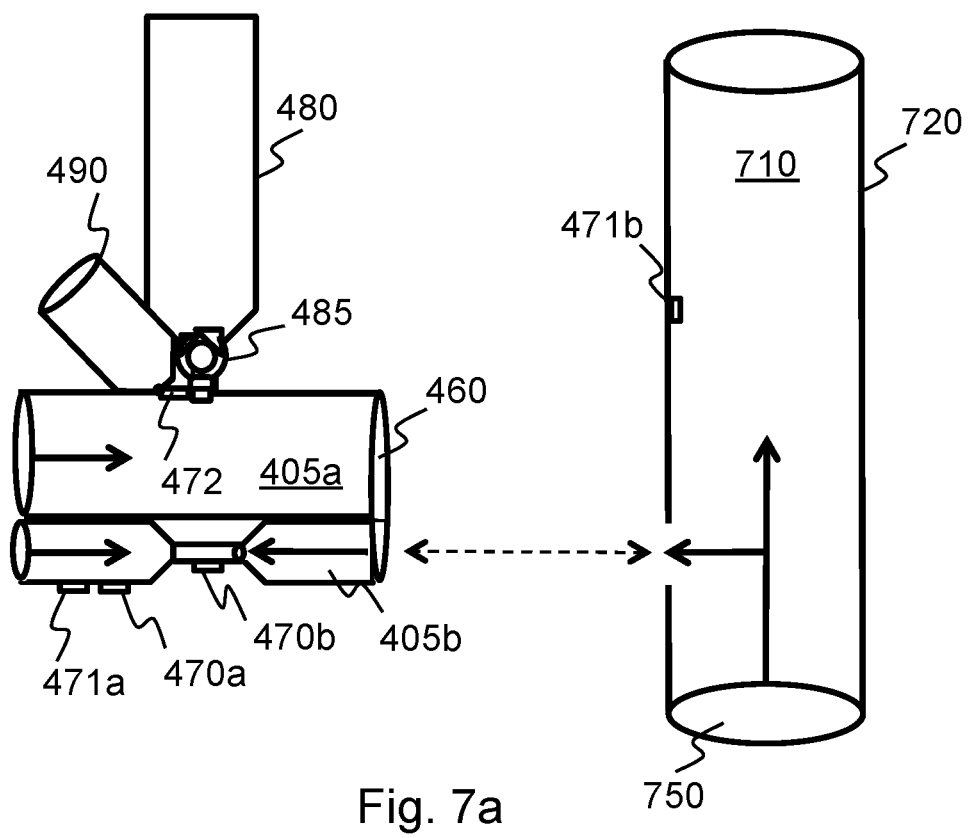
FIG. 7a shows a schematic drawing of a portable inhalator device of an example embodiment.

FIG. 7a shows a schematic drawing of a portable inhalator device 110 of an example embodiment. In an embodiment, a plurality of sensors 470a-b, 471a-b, 472 is included. At least two sensors 470a-b, 471a-b are implemented. In an embodiment, the device 110 may communicate with a plurality of sensors 470-472, both internal and external sensors, and of a plurality of users. In an embodiment, the sensor may also comprise a camera for capturing multimedia data to be submitted to the server apparatus 130, 131 for determination of preliminary trauma information or for creating multimedia data.

The portable inhalator device 110 comprises a housing comprising a mouthpiece 460 for a user and a gas conduit 405a-b coupled to the mouthpiece 460 and configured to guide inhaling and exhaling gas flow within the device 110.

The gas conduit 405 of FIG. 4 may comprise a first gas conduit 405a, and a second gas conduit 405b, as shown in FIG. 7.

A third gas conduit 710 may be connected with the gas conduit 405, as shown in FIG. 7.

The portable inhalator device 110 may further comprise at least one pressure sensor 470a-b configured to monitor the gas flow in the second gas conduit part 405b and to provide pressure differential signal for indicating direction of the gas flow through the gas conduit 405a-b.

In embodiment, the pressure sensor 470a-b may comprise a plurality of pressure sensors 470a, 470b. The pressure sensor(s) 470a-b are configured to provide direction and volume of the flow that may be used to determine characteristics of breathing and dosing of the drug (timing and amount).

The portable inhalator device 110 further comprises a detection sensor 471a configured to monitor the gas flow in the second gas conduit part 405b and to provide characteristics signal for indicating composition of the gas flow through the second gas conduit part 405b.

The portable inhalator device 110 may further comprise another detection sensor 471b configured to monitor the gas flow in a third gas conduit part 710 of the gas conduit 405a-b, 710 and to provide characteristics signal for indicating composition of the gas flow through the third gas conduit part 710.

The portable inhalator device 110 further comprises a dispenser 485 configured to dispense a drug to the first gas conduit part 405a.

In an embodiment, the portable inhalator device 110 further comprises a detection sensor 471a configured to monitor the gas flow in the second gas conduit part 405b and to provide characteristics signal for indicating composition of the gas flow through the second gas conduit part 405b.

In an embodiment, the second gas conduit part 405b may comprise a venture pipe as shown in FIG. 7a configured to determine flow speed of a fluid (such as gas flow) within the venture pipe based on pressure difference information received and generated based on at least one of the sensors 470a-b, 471a. The second gas conduit part 405b may also be used to measure diagnostics information of a fluid (such as gas flow or phlegm) within the second gas conduit part 405b based on diagnostics information received and generated based on at least one of the sensors 470a-b, 471a.

In an embodiment, the first gas conduit part 405a may be opened when inhaling and the second gas conduit part 405b may be closed.

In an embodiment, the first gas conduit part 405a and the second gas conduit part 405b may be arranged to be combined as an inhaling gas conduit part 405a-b.

In an embodiment, the second gas conduit part 405b may be opened when exhaling and the first gas conduit part 405a may be closed.

In an embodiment, the second gas conduit part 405b and the first gas conduit part 405a may be arranged to be combined as an exhaling gas conduit part 405a-b.

In an embodiment, the second gas conduit part 405b may be opened when exhaling and the first gas conduit part 405a may be closed.

In an embodiment, a third gas conduit part 710 is arranged in connection to at least one of the first and the second gas conduit 405a-b.

In an embodiment, a user (a patient) inhales a medicine from the drug container 480 and simultaneously peak inspiratory flow (PIF) is measured by at least one sensor 471, 472 to define information of drug inhaling.

In an embodiment, metadata may be received from a server apparatus 130-132. The metadata may comprise data of medical history, genetic analysis information, seasonal information, such as time of the year, manner of living, activity, and so on.

The metadata may be used for triggering a request for the device 110 to perform a PEF measurement and in response the PEF measurement trigger a PEF analysis and further provide a questionnaire to the user and/or provide instructions on physical, mental, medical or nutrition information. The information may be shared to the network of the user, such as the doctor and/or therapist, for example.

In an embodiment, the dispenser 485 is controlled to dispense the drug to the gas conduit 405a based on the dispense control information.

In an embodiment, if it is detected based on the sensor information from sensors 471b, 472 that inhaling of the user is weak (e.g. by 30%) or it is detected based on sensors 471a, 470a-b that indicates that, for example, the user is not capable of inhaling gas flow with the drug to lungs of the user without assistance.

In an embodiment, an adaptor 720 is removably attached to the gas conduit part 405a-b of the device 110. The adaptor 720 may be removable and exchangeable to the device 110 to selectively open or close at least one of the gas conduit parts 405a-b and the gas conduit status is detected and provided to the service system.

In an embodiment, when exhaling, the adaptor 720 is connected to the mouthpiece 460 as illustrated by the dashed arrow. The adaptor 720 comprises an aperture arranged and aligned next to the second gas conduit part 405b so that exhaled flow is passed to the second gas conduit part 405b for measurement. A mouthpiece 750 of the adaptor 720 is then used by the user to exhale into the device 110. The adaptor 720 and/or the mouthpiece 460 may have mechanical locking means to removably attach the elements together in correct position with each other. During exhaling, the exhaled flow speed, pressure, volume and/or composition of the exhaled gas flow may be measured by the sensors 470-471. Sensor 471b (optional) may be used to measure exhaled gas flow not entering the second gas conduit part 405b for measurement.

In an embodiment, when inhaling, the adaptor 720 is disconnected from the mouthpiece 460 as illustrated by the dashed arrow. A mouthpiece 460 of the device 110 is then used by the user to inhale gas flow through the first 405a and the second gas conduit part 405b of the device 110. The first gas conduit part 405a may be used for dispensing drug from the container 480 using the dispenser 485 and if needed, the assistance 490. Simultaneously, during inhaling, the inhaled flow speed, pressure, volume and/or composition of the inhaled gas flow may be measured by the sensors 470-472.

In an embodiment, negative values are determined for the pressure differential signal for indicating inhalation of the gas flow through the gas conduit 405a, 405b and positive values are determined for the pressure differential signal for indicating exhalation of the gas flow through the gas conduit 405b, 710. Peak expiratory flow (PEF) information may be determined based on the positive values of the pressure differential signal.

The device 110 may comprise at least one drug container 480, wherein the drug container(s) are operationally connected to the dispenser 485 for conveying drugs between the drug container(s) 480 and the dispenser 485.

Figure 7B:
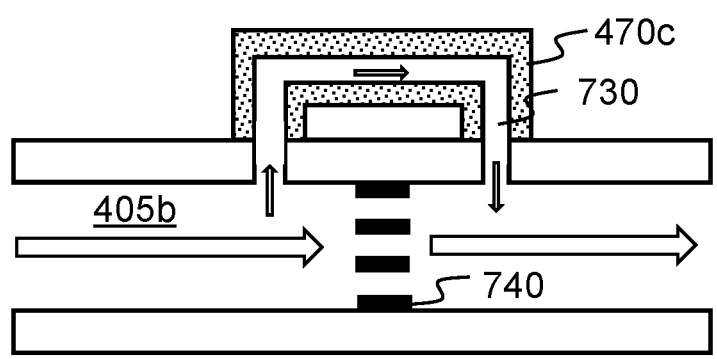

FIG. 7b shows a schematic drawing of the second gas conduit part 405b that illustrates an alternative to the venture pipe as shown in FIG. 7a.

The second gas conduit part 405b may be configured to determine flow speed of a fluid (e.g. a gas flow) within the conduit part 405b based on pressure difference information received and generated based on at least one sensors 470c.

The second gas conduit part 405b comprises a main pass channel wherein at least one pressure drop element 740 is arranged to limit or restrict the incoming gas flow, as illustrated.

The sensor 470c is configured to measure the bypass channel 730 that guides a portion of the incoming gas flow through it and bypassing the pressure drop element 740.

A flow restrictor 740 generates a pressure drop, which guides a small proportion of the gas through the bypass channel 730. The pressure drop element 740 ensures that the resulting differential pressure measured by the sensor 470c is less susceptible to changes to the inlet conditions. Also important is the arrangement of the bypass tapping ports. By using inertia effects and minimizing the bypass flow, an intelligent bypass channel design will ensure a clean gas flow to the sensor 470c.

Using a bypass configuration helps to simplify the manufacturing process too. It allows for the flow element to be molded and assembled independently of the sensor 470c.

Without in any way limiting the scope, interpretation, or application of the claims appearing below, a technical effect of one or more of the example embodiments disclosed herein is improved method and apparatus for providing collaborative patient information.

Another technical effect of one or more of the example embodiments disclosed herein is improved measurement of drug influence. Another technical effect of one or more of the example embodiments disclosed herein is real-time follow-up of drug dosing and its effectiveness. Another technical effect of one or more of the example embodiments disclosed herein is an improved quality of drug treatment of the patient trauma. Another technical effect of one or more of the example embodiments disclosed herein is an improved communication between the patient and the health care. Another technical effect of one or more of the example embodiments disclosed herein is an improved priority determination for directing patients to visit health care or receive further treatment. Another technical effect of one or more of the example embodiments disclosed herein is improved user experience and life quality for the patient. Another technical effect of one or more of the example embodiments disclosed herein is improved accuracy of the patient information relating to a trauma. Another technical effect of one or more of the example embodiments disclosed herein is that a plurality of users linked with the patient's trauma rehabilitation may have up-to-date access to all patient information relevant for the rehabilitation process. Another technical effect of one or more of the example embodiments disclosed herein is that external users required to have information of the progress of the rehabilitation process and its progress may have access to the latest information in a dynamic way by giving permissions to such external users to certain parts of the collaborative patient information. Another technical effect of one or more of the example embodiments disclosed herein is that only a single system is need for all and no complex apparatuses are needed, and a wide variety of mobile devices, smartphones, tablets and computers may be used to provide more simple system.

In an embodiment, each user may be identified by a user identifier, such as a social security number or personal e-mail address that may be verified when a user profile is created to the system. At least one authorized user (e.g. the origin user for the data) for the collaborative patient record may define access rights for other users within the system for certain parts of the information within the collaborative patient record.

If desired, the different functions discussed herein may be performed in a different order and/or concurrently with each other. Furthermore, if desired, one or more of the before-described functions may be optional or may be combined.

Although various aspects of the invention are set out in the independent claims, other aspects of the present disclosure comprise other combinations of features from the described embodiments and/or the dependent claims with the features of the independent claims, and not solely the combinations explicitly set out in the claims.

It is also noted herein that while the foregoing describes example embodiments of the present disclosure, these descriptions should not be viewed in a limiting sense. Rather, there are several variations and modifications, which may be made without departing from the scope of the present disclosure as defined in the appended claims.

However, claimed embodiments do not constitute a method step for treatment of the human or animal body by surgery or therapy. No functional relationship exists between the steps related to apparatus and any therapeutic effect of the apparatus on the body.

The invention claimed is:

1. A portable inhalator device comprising:
a housing comprising a mouthpiece for a user;
a gas conduit coupled to the mouthpiece and configured to guide inhaling and exhaling gas flow within the device;
a pressure sensor configured to monitor gas flow in the gas conduit and to provide pressure differential signal for indicating both inhalation and exhalation direction of the gas flow through the gas conduit;
a detection sensor configured to monitor the gas flow in the gas conduit and to provide a characteristics signal for indicating a composition of the gas flow through the gas conduit;
a dispenser configured to dispense a drug to the gas conduit;
a system for sensing an altitude of the device;
at least one memory including computer program code;
the at least one memory and the computer program code configured to, with at least one processor, cause the device to:
receive the pressure differential signal from the pressure sensor;
determine dispense control information based on the pressure differential signal, the dispense control information comprising at least one of the following:
timing of dispense; and
amount of the drug to be dispensed;
control the dispenser to dispense the drug to the gas conduit based on the dispense control information;
receive the characteristics signal indicating composition of the exhaled gas flow from the detection sensor;
determine adjusted control information based on the characteristics signal and the altitude of the device; and
adjust the dispenser to dispense the drug to the gas conduit based on the adjusted control information.

2. The portable inhalator device of claim 1, wherein the at least one memory and the computer program code are further configured to, with the at least one processor, cause the device to:
determine negative values for the pressure differential signal for indicating inhalation of the gas flow through the gas conduit.

3. The portable inhalator device of claim 1, wherein the at least one memory and the computer program code are further configured to, with the at least one processor, cause the device to:
determine positive values for the pressure differential signal for indicating exhalation of the gas flow through the gas conduit.

4. The portable inhalator device of claim 3, wherein the at least one memory and the computer program code are further configured to, with the at least one processor, cause the device to:
determine peak expiratory flow (PEF) information based on positive values of the pressure differential signal.

5. The portable inhalator device of claim 1, further comprising a drug container, wherein the drug container is operationally connected to the dispenser for conveying the drug between the drug container and the dispenser.

6. The portable inhalator device of claim 1, further comprising a plurality of drug containers, wherein the drug containers are operationally connected to the dispenser for conveying drugs between the plurality of drug containers and the dispenser.

7. The portable inhalator device of claim 1, wherein the at least one memory and the computer program code are further configured to, with the at least one processor, cause the device to:
store user history information comprising at least one of the following:
the dispense control information;
the characteristics signal or characteristics information defined based on the characteristics signal; and
the adjusted control information.

8. The portable inhalator device of claim 7, wherein the at least one memory and the computer program code are further configured to, with the at least one processor, cause the device to:
store device history information comprising at least one of the following:
information on amount of the drug dispensed; and
information on amount of the drug remaining.

9. The portable inhalator device of claim 8, wherein the at least one memory and the computer program code are further configured to, with the at least one processor, cause the device to:
receive container information comprising information on amount of drug within the drug container; and
determine amount of remaining drug within the drug container based on the container information and the device history information.

10. The portable inhalator device of claim 1, further comprising an inhaling assistance element, wherein the inhaling assistance element is configured to generate additional inhaling gas flow to the gas conduit.

11. The portable inhalator device of claim 10, wherein the at least one memory and the computer program code are further configured to, with the at least one processor, cause the device to:
determine inhaling assistance control information based on the pressure differential signal, the inhaling assistance control information comprising at least one of the following:
timing of inhaling assistance; and
amount of the inhaling assistance; and
control the inhaling assistance element to generate additional inhaling gas flow to the gas conduit based on the inhaling assistance control information.

12. The portable inhalator device of claim 1, further comprising a data connection to a server apparatus, wherein the portable inhalator device is configured to send data representing the pressure and detection signals over the data connection to the server apparatus.

13. The portable inhalator device of claim 12, wherein instructions and orders for medication are dynamically adjusted and updated based on the data sent by the portable inhalator device.

14. A computer program stored in a memory, comprising computer executable program code configured to control a portable inhalator device, wherein the portable inhalator device comprising:
a processor;
a housing comprising a mouthpiece for a user; a gas conduit coupled to the mouthpiece and configured to guide inhaling and exhaling gas flow within the device;
a pressure sensor configured to monitor the gas flow in the gas conduit and to provide pressure differential signal for indicating both inhalation and exhalation direction of the gas flow through the gas conduit;
a detection sensor configured to monitor the gas flow in the gas conduit and to provide characteristics signal for indicating composition of the gas flow through the gas conduit; and
a dispenser configured to dispense a drug to the gas conduit;
a system for sensing an altitude of the device;
wherein the computer executable program code is executed by the processor to:
receive the pressure differential signal from the pressure sensor;
determine dispense control information based on the pressure differential signal, the dispense control information comprising at least one of the following: timing of dispense; and
amount of the drug to be dispensed;
control the dispenser to dispense the drug to the gas conduit based on the dispense control information;
receive the characteristics signal indicating composition of the exhaled gas flow from the detection sensor;
determine adjusted control information based on the characteristics signal and the altitude of the device; and
adjust the dispenser to dispense the drug to the gas conduit based on the adjusted control information.

15. A computer-implemented method for a portable inhalator device, wherein the portable inhalator device comprising a housing comprising a mouthpiece for a user; a gas conduit coupled to the mouthpiece and configured to guide inhaling and exhaling gas flow within the device; a pressure sensor configured to monitor the gas flow in the gas conduit and to provide pressure differential signal for indicating both inhalation and exhalation direction of the gas flow through the gas conduit; a detection sensor configured to monitor the gas flow in the gas conduit and to provide characteristics signal for indicating composition of the gas flow through the gas conduit; a dispenser configured to dispense a drug to the gas conduit; and a system for sensing an altitude of the device; the method comprising:
receiving the pressure differential signal from the pressure sensor;
determining dispense control information based on the pressure differential signal, the dispense control information comprising at least one of the following:
timing of dispense; and
amount of the drug to be dispensed;
controlling the dispenser to dispense the drug to the gas conduit based on the dispense control information;
receiving the characteristics signal indicating composition of the exhaled gas flow from the detection sensor;
determining adjusted control information based on the characteristics signal and the altitude of the device; and
adjusting the dispenser to dispense the drug to the gas conduit based on the adjusted control information.

16. The method of claim 15, further comprising:
generating patient trauma information based on the characteristics signal;
transmitting the patient trauma information to a server apparatus;
generating patient rehabilitation information based on the patient trauma information;
associating the patient trauma information and the patient rehabilitation information with a patient identifier to provide a collaborative patient record;
automatically determining adjusted control information based on the collaborative patient record; and
transmitting the adjusted control information for the portable inhalator device.

17. The method of claim 15, further comprising:
transmitting the characteristics signal to a server apparatus;
generating patient trauma information based on the characteristics signal;
generating patient rehabilitation information based on the patient trauma information;
associating the patient trauma information and the patient rehabilitation information with a patient identifier to provide a collaborative patient record;
automatically determining adjusted control information based on the collaborative patient record; and
transmitting the adjusted control information for the portable inhalator device.

18. A portable inhalator device comprising:
a housing comprising a mouthpiece for a user;
a gas conduit coupled to the mouthpiece and configured to guide inhaling and exhaling gas flow within the device;
a pressure sensor configured to monitor the gas flow in the gas conduit and to provide pressure differential signal for indicating both inhalation and exhalation direction of the gas flow through the gas conduit;
a detection sensor configured to monitor the gas flow in the gas conduit and to provide characteristics signal for indicating composition of the gas flow through the gas conduit for diagnosing a disease, impurities or infection within a body system of the patient;
a dispenser configured to dispense a drug to the gas conduit;
a system for sensing an altitude of the device;
at least one memory including computer program code;
the at least one memory and the computer program code configured to, with the at least one processor, cause the device to:
receive the pressure differential signal from the pressure sensor;
determine dispense control information based on the pressure differential signal, the dispense control information comprising at least one of the following:
timing of dispense; and
amount of the drug to be dispensed;
control the dispenser to dispense the drug to the gas conduit based on the dispense control information;
receive the characteristics signal from the detection sensor during exhaling;
determine adjusted control information based on the characteristics signal and the altitude of the device; and adjust the dispenser to dispense the drug to the gas conduit based on the adjusted control information.

19. The portable inhalator device of claim 1, further comprising:
- a second gas conduit;
- at least one other pressure sensor configured to provide a pressure differential signal indicating flow through the second gas conduit;
- at least one other detection sensor configured to provide a signal indicating a composition of the gas flow through the second gas conduit,
- wherein the second gas conduit is configured to measure diagnostics information of a fluid within the second gas conduit based on diagnostics information received and generated from the signals of at least one of the other pressure or detection sensors.

* * * * *